United States Patent

Sohn

[11] Patent Number: 5,873,891
[45] Date of Patent: Feb. 23, 1999

[54] STAPLE AND THREAD ASSEMBLY PARTICULARLY FOR USE IN POWER-DRIVEN STAPLERS FOR MEDICAL SUTURING

[75] Inventor: Ze'ev Sohn, Modiin, Israel

[73] Assignee: Influence Medical Technologies, Ltd., Herzelia, Israel

[21] Appl. No.: 946,335

[22] Filed: Oct. 7, 1997

Related U.S. Application Data

[63] Continuation of Ser. No. 572,682, Dec. 14, 1995, Pat. No. 5,674,247.

[30] Foreign Application Priority Data

Dec. 14, 1994 [IL] Israel .......................................... 119985

[51] Int. Cl.⁶ ........................................................ A61B 17/08
[52] U.S. Cl. .......................... 606/219; 606/219; 606/232
[58] Field of Search .................................... 606/232, 219, 606/320, 213, 75, 73, 72, 187

[56] References Cited

U.S. PATENT DOCUMENTS

| | | | |
|---|---|---|---|
| 5,405,359 | 4/1995 | Pierce | 606/232 |
| 5,527,342 | 6/1996 | Pietrzak et al. | 606/232 |
| 5,674,247 | 10/1997 | Sohn | 606/219 |

*Primary Examiner*—Michael Buiz
*Assistant Examiner*—Tina T. D. Pham
*Attorney, Agent, or Firm*—Levisohn, Lerner, Berger & Langsam

[57] ABSTRACT

A staple and thread assembly to be driven into the bone by a power-driven stapler while the thread is attached thereto, the stapler having a head section at its forward end formed with a pointed tip for penetrating the bone when driven into it, and a shank section rearwardly of the head. The longitudinal axis of the shank section is offset from the axis of the head section and is formed with a pair of transverse holes through which the thread is secured such that the thread exits from the holes. The head section forms a protective shroud shielding the thread when driven with the staple into the bone. The thread is secured to the shank section of the staple at a point closer to the staple tip than the rear end of the staple. The staple is constructed from a metal possessing shape memory characteristics, and deforms from a straight configuration at room temperature, to a curved configuration upon being subject to body heat upon implantation into the body. The suture thread is secured to the shank section and, preferably, a recess is provided to the shank section to protect the thread.

15 Claims, 2 Drawing Sheets

STAPLE AND THREAD ASSEMBLY PARTICULARLY FOR USE IN POWER-DRIVEN STAPLERS FOR MEDICAL SUTURING

This application is a continuation of application Ser. No. 08/572,682 filed Dec. 14, 1995 which application is now: U.S. Pat. No. 5,674,247 and, claims the priority of Israeli Application Serial No. 119985, filed Dec. 14, 1994 now abandoned.

The present application claims the priority pursuant to 35 U.S.C. §119 of Israeli Patent Application Serial No. 111985, filed Dec. 14, 1994. The present application also claims priority under 35 U.S.C. §120 to U.S. patent application Ser. No. 08/572,682, now issued as U.S. Pat. No. 5,674,247 on Oct. 7, 1997.

BACKGROUND OF THE INVENTION

The present invention relates to a staple and thread assembly particularly useful in power-driven staplers for medical suturing. The invention is especially useful in treating urinary stress incontinence in a manner as described in our prior Patent Application filed in Israel, Serial No. 103737 filed Nov. 13, 1992, and is therefore described below with respect to such an application, but it will be appreciated that the invention could advantageously be used in other applications as well. The teachings of that application are incorporated herein by reference.

SUMMARY OF THE INVENTION

As described in our Patent Application Serial No. 103737, filed Nov. 13, 1992, urinary stress incontinence, i.e., the inability to control urination from the bladder, is a distressing problem for more than ten percent of elderly women as well as for many young women, and many surgical operations have been devised to correct this condition. The above-cited patent application discloses a technique to avoid a surgical incision through the abdominal wall. A staple and a suture thread are ejected through the vaginal wall of the subject to enter the pubic bone, and the suture thread is used for attaching and adjusting the location of the bladder neck and the proximal urethra of the subject to the posterior wall of the pubic bone. Such a technique thus eliminates the need for an abdominal incision and minimizes damage to the anterior vaginal wall. By ejecting the anchor/stapler into a bone, the need to drill a hole in the bone is eliminated, as required in previously-known techniques.

The present invention relates primarily to an improved staple and thread assembly particularly useful in the above-described technique, but also useful in other applications, such as in treating a recurrent shoulder dislocation condition.

According to the present invention, there is provided a staple and thread assembly to be driven into an object by a power-driven stapler while the thread is attached thereto, the stapler having a head section at its forward end formed with a pointed tip for penetrating the object when driven into it, and a shank section rearwardly of the head; characterized in that the shank section is recessed inwardly of the head section and is formed with a transverse hole in which the thread is secured such that the thread exits from the hole perpendicularly to the longitudinal axis of the staple, and the head section forms a protective shroud shielding the thread when driven with the staple into the object.

According to further features in the preferred embodiment of the invention described below, the shank section is formed with a closely-spaced pair of the transverse holes separated by a web, the thread being passed through one of the holes, looped around the web, and passed out through the other hole such that it is secured to the shank by the web and extends outwardly therefrom perpendicularly to the longitudinal axis of the staple while its point of securement to the staple is shielded by the head section of the staple. In addition, the point of securement of the thread to the staple is closer to the pointed tip of the head section than to the rear end of the shank section.

Many metal alloys are known possessing shape memory characteristics, i.e., the ability of being deformed from an original, heat-stable configuration to a second, heat-unstable configuration such that application of heat alone will cause the article to revert, or to attempt to revert, from its heat-unstable configuration to its original heat-stable configuration. This "memory" characteristic is a consequence of the alloy undergoing a reversible transformation from a martensitic state at room temperature to an austenitic state when heated to the body temperature. One material known for this purpose is a nickel/titanium/vanadium alloy described, for example, in U.S. Pat. No. 4,505,767; other materials having this characteristic are also known.

According to still further features in the described preferred embodiment, the staple is made of a shape memory alloy which is formable, non-elastic, and straight at room temperature, and is curved and elastic when heated by a person's body temperature. Preferably, the shape memory alloy is in the martensitic state at about room temperature and reverts to the austenitic state when heated to about the body temperature.

It will thus be seen that when a staple and thread assembly constructed in accordance with the foregoing features is driven into the object (e.g., the pubic bone when used for treating a female subject for urinary-stress incontinence in accordance with the method of the above-cited patent application), the protective shroud formed by the recess at the point of attachment of the thread to the staple protects the thread from damage at the time it is driven into the bone by the power-driven stapler. In addition, after the staple has penetrated the pubic bone, body heat transforms the staple from its original straight form (at the time it was driven into the bone) to a curved form, thereby securely fixing the staple and thread within the pubic bone. This manner of fixing the thread is further enhanced by securing the thread to the shank section of the staple at a point closer to the pointed tip, rather than to the rear end of the staple, since, by securing the thread nearer to the pointed tip, a pull-out force would tend to rotate the staple and thereby to more securely anchor it to the bone. This feature, as well as the use of a shape memory alloy for the staple causing it to assume a curved, elastic condition in the body, also decreases the possibility that a pull-out force might sever the thread by bringing it into contact with the edges of the staple.

The invention further provides a power-driven stapler including the novel staple and thread assembly, and also a method of treating a female subject for urinary stress incontinence by the use of such a staple and thread assembly.

Further features and advantages of the invention will be apparent from the description below.

BRIEF DESCRIPTION OF THE DRAWINGS

The invention is herein described, by way of example only, with reference to the accompanying drawings, wherein.

DETAILED DESCRIPTION OF THE DRAWINGS AND THE PREFERRED EMBODIMENTS

Figure 1:
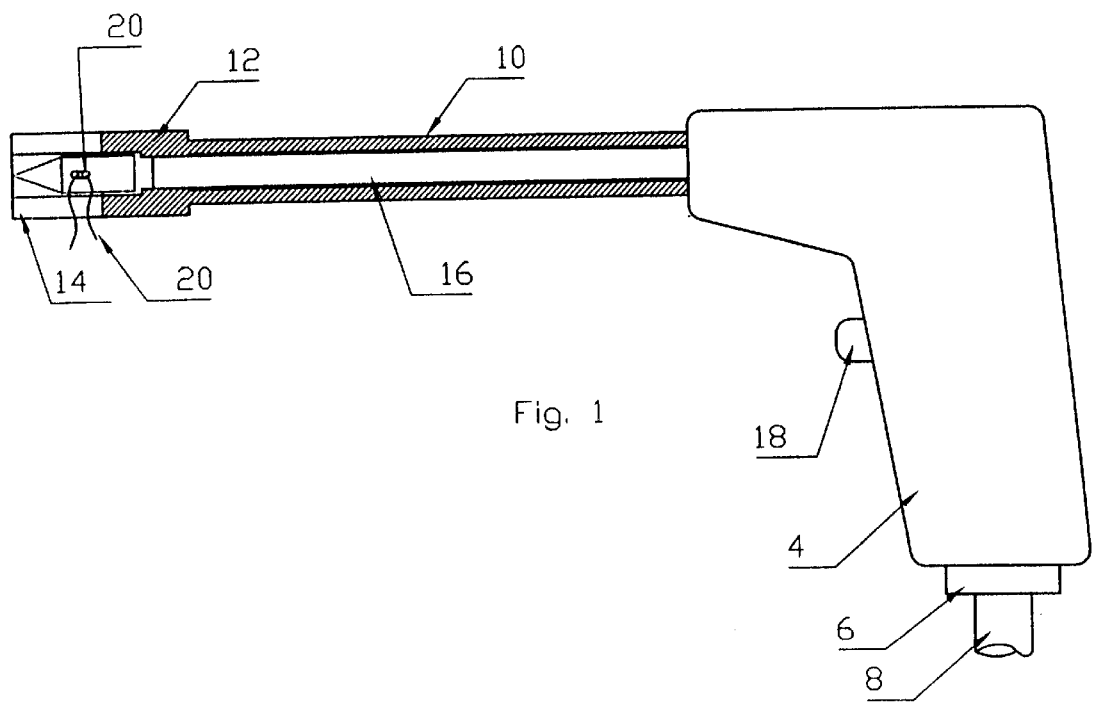
FIG. 1 illustrates a side view of one form of power stapler device useful for ejecting the novel staple and thread assembly of the present invention.

The stapler device illustrated in FIG. 1 is of substantially the same construction as described in our above-cited U.S. patent application. That teaching is incorporated herein by reference. It comprises a housing, generally designated 2, including a handle 4 which is manually grippable by the user. The illustrated stapler device is pneumatically powered, and therefore includes a connector 6 at the bottom of the handle 4 for attaching thereto a tube 8 connectible to a source of pressurized air. Housing 2 further includes an elongated barrel 10 having a straight guide 12 at its end for the staple 20 to be ejected. Ejection of the staple 20 is effected by an ejector pin 16 which is driven into sharp impact against the base of the staple 20 by the air pressure supplied through the pressurized air tube 8. Handle 4 includes a trigger 18 which, when depressed, applies an air pressure pulse to ejector pin 16 to cause it to impact against the base of staple 20 and thereby to eject the staple out through the end of straight guide 12.

As also described in the above-cited patent U.S. application, the staple 20 ejected from the guide at the end of barrel 10 has a suture thread 30 secured to the staple and ejected with it. When the power-driven stapler, and the staple and thread assembly driven thereby, are used for treating urinary stress incontinence, the staple is driven through the patient's vaginal wall and into the pubic bone. The thread 30 is then used for securing the bladder neck and the proximal urethra of the subject to the posterior or upper wall of the pubic bone.

Figure 2:
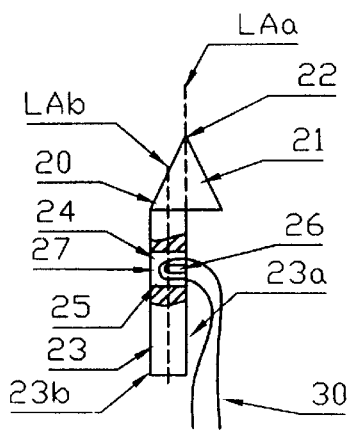
FIG. 2 is a side elevational view, partly in cross section, illustrating one form of staple and thread assembly constructed in accordance with the present invention, the assembly being shown in its condition at room temperature.
Figure 3:
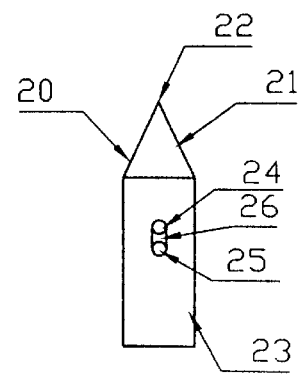
FIG. 3 is a top plan view of the staple and thread assembly of FIG. 2.
Figure 4:
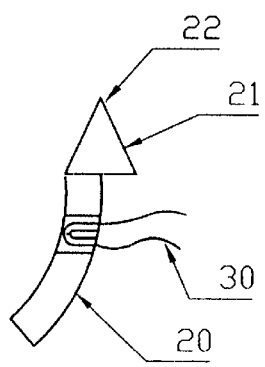
FIG. 4 is a side elevational view illustrating the staple of FIGS. 2 and 3 in its curved condition after having been driven into the pubic bone of a subject and heated by the subject's body heat.

FIGS. 2–4 illustrate one form of novel assembly including a staple 20 and a thread 30 secured thereto constructed in accordance with the present invention and providing important advantages when used in the above-described technique, as will be set forth more particularly below.

Thus, the staple 20 illustrated in FIGS. 2–4 includes a head section 21 at its forward end formed with a pointed tip 22 for penetrating the object (e.g., the pubic bone) into which it is driven, and a shank section 23 rearwardly of the head section. In the construction illustrated in FIGS. 2–4, the longitudinal axis LAs of the shank section 23 is offset from the longitudinal axis LAa of the head section 21 such that the shank section is offset at one side 23a from the corresponding side of the head section 21, whereas the opposite side 23b of the shank section is flush with the other side of the head section.

The shank section 23, adjacent to its juncture with the head section 21, is formed with a pair of closely-spaced holes 24, 25 extending perpendicularly to the axis LAs of the shank section. The two holes are separated by a web portion 26 which is recessed at one side, namely side 23b of the shank section, as shown at 27 in FIG. 2. This recess accommodates the thickness of the thread so that the thread does not extend beyond side 23b.

The suture thread 30 is passed through hole 24, looped around the recessed end of web 26, and exits from hole 25, as shown particularly in FIG. 2.

The staple 20 illustrated in FIGS. 2–4 is preferably made of a shape memory alloy which is formable, non-elastic and straight at room temperature (as shown in FIGS. 2 and 3) and which becomes elastic and curved when heated to a higher temperature, e.g., the subject's body temperature (as shown in FIG. 4). Preferably, the shape memory alloy is in the martensitic state at room temperature (FIGS. 2, 3) and reverts to the austenitic state when heated by the body temperature (FIG. 4). Such shape memory alloys are known, as described for example in U.S. Pat. No. 4,505,767.

FIGS. 5a–5e illustrate how the staple and thread assembly of the present invention is driven by the stapler device of FIG. 1 into the pubic bone (or other bone) of a subject, e.g., during a treatment for urinary stress incontinence as described in the above-cited U.S. patent application.

Figure 5A:
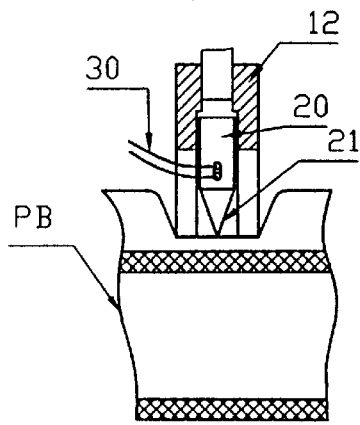
FIGS. 5a–5e illustrate the various stages of the stapler used for ejecting the staple and thread assembly of FIGS. 2–4, the staple and a bone. The figures show the driving of the staple and thread assembly into the pubic bone of a subject; and, FIGS. 6 and 7 are side plan views illustrating possible variations in the construction of the staple and thread assembly.
Figure 5B:
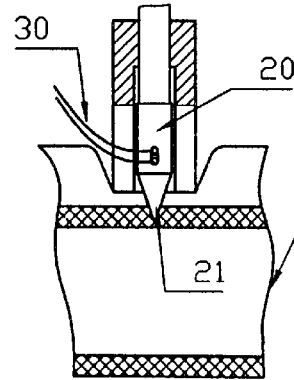
Figure 5C:
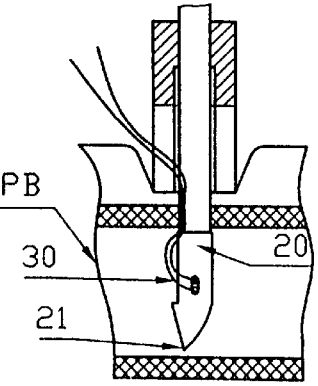
Figure 5D:
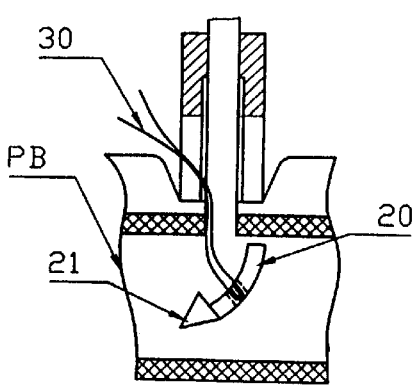

Thus, FIG. 5a illustrates the staple in its original straight condition as illustrated in FIGS. 2 and 3, i.e., in the martensitic state at room temperature wherein it is formable and non-elastic so that it can be inserted and retained in the straight guide 12 of the power-driven stapler of FIG. 1. While the staple is in its straightened condition, and with the thread 30 looped around the web portion 26, the staple is power-driven by ejector pin 16 (FIG. 1) through barrel 10 and straight guide 12 such that the pointed end 22 of the staple penetrates through the pubic bone PB (FIGS. 5a–5c). After it penetrates the pubic bone, the body heat transforms the staple 20 from its martensitic state to its austenitic state, wherein it becomes curved. (FIG. 5d). The thread 30 is then pulled in an outward direction with respect to the pubic bone, whereupon the staple rotates to the position illustrated in FIG. 5e, thereby firmly anchoring the staple in the bone. The thread 30 may then be used for securing the bladder neck and proximal urethra to the pubic bone.

This construction for securing thread 30 to the staple 20 provides a number of important advantages. Thus, the offset construction of shank 23 at the point of securement of the thread thereto results in the head section 21 forming a protective shroud which shields the thread 30, particularly its point of securement via the two holes 24, 25 and the web 26, to the shank 23, thereby protecting the thread and its point of attachment against damage at the time the staple and thread assembly are driven by the power stapler through the bone. The looped end of the thread 30 is also protected by the recessed configuration of the web 26 as shown at 27.

Figure 5E:
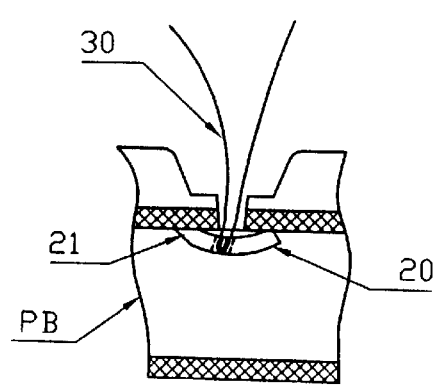

In addition, using a shape memory alloy for the staple as described above enables the staple to be in its straight form when driven through the bone, and causes the staple to assume its curved form as shown in FIG. 4, a consequence of the body temperature effecting the martensite to austenite change. The change of staple shape occurs after it is driven into the bone, thereby securely anchoring the staple to the bone. In addition, by forming the point of attachment of thread 30 to the staple, at a point closer to the pointed tip 22 of the staple than the rear end of the shank, a pull-out force turns the staple within the bone, as shown in FIGS. 5d and 5e, thereby further securely anchoring the staple to the bone. In addition, the described structure decreases the possibility that a pull-out force will cause the thread to engage an edge of the staple such that it may become accidentally severed.

Figure 6:
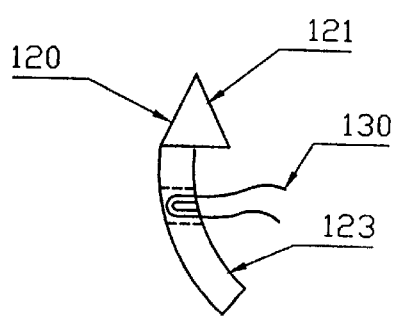
Figure 7:
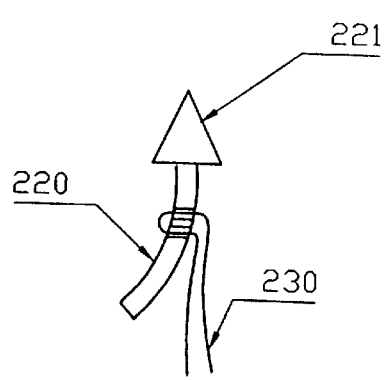

FIGS. 6 and 7 illustrate variations in the construction of the staple, therein designated 120 and 220, respectively. In the modification illustrated in FIG. 6, the staple 120, when subjected to body heat and therefore when in its austenitic state, becomes curved such that the recess shrouded by the head section 121 is on the concave face of the shank section 123, rather than on its convex face as in FIG. 4. In the modification illustrated in FIG. 7, the recess defined by the head section 221, for producing the protective shroud shielding the thread 230 at its point of attachment to the shank section 223, is formed on both sides of the shank section, rather than on only one side as in FIG. 4. In all other respects, the staple and thread assemblies illustrated in FIGS. 6 and 7 are otherwise constructed and used in the same manner as described above with respect to FIGS. 1–5e.

While the invention has been described with respect to several preferred embodiments, it will be appreciated that these are set forth merely for purposes of example, and that many variations may be made. For example, the stapler could be spring-loaded, in which case the spring would be first manually compressed and then released by pressing a trigger to eject the staple. Other ways may be used, as known in the art, for converting energy stored in a spring or in a compressed gas to drive the staple. In addition, the barrel of the stapler could be pre-curved, or could be flexible enabling it to be curved, as may be desired or required for specific applications. While the invention is particularly useful for treating urinary stress incontinence in the manner described above, the invention could also be used in other applications, e.g., for treating a recurrent dislocation of the shoulder.

Having described this invention with regard to specific embodiments, it is to be understood that the description is not meant as a limitation since further variations or modifications may be apparent or may suggest themselves to those skilled in the art. It is intended that the present application cover such variations and modifications as fall within the scope of the appended claims.

I claim as follows:

1. A staple and thread assembly for use in medical suturing, comprising:

a staple having a head section having a longitudinal axis, LAa, and a shank section having a longitudinal axis, LAs, said head section being at said staple's ward end and being formed with a pointed tip for penetrating a bone when driven into the bone, said shank section being located immediately rearwardly of said head section, said LAa of said head section being laterally offset from said LAs of said shank section such that said head section asymmetrically overhangs said shank section when said staple is driven into the bone.

2. A staple and thread assembly as claimed in claim 1, further comprising suture holding means for attaching suture thread to said staple, said suture holding means comprising a hole in said staple.

3. A staple and thread assembly as claimed in claim 1, further comprising suture thread attached to said staple.

4. A staple and thread assembly as claimed in claim 2, further comprising suture thread attached to said staple.

5. A staple and thread assembly as claimed in claim 1, wherein said shank section is offset with respect to said head section on only one side of said shank section.

6. A staple and thread assembly as claimed in claim 3, wherein said shank section is offset with respect to said head section on only one side of said shank section.

7. A staple and thread assembly as claimed in claim 1, wherein one side of said shank section of said staple is flush with a first side of said head section, and the opposite side of said shank section is offset inwardly with respect to a second side of said head section.

8. A staple and thread assembly as claimed in claim 3, wherein one side of said shank section of said staple is flush with a first side of said head section, and the opposite side of said shank section is offset inwardly with respect to a second side of said head section.

9. A staple and thread assembly as claimed in claim 1, wherein said shank section is offset with respect to said head section on both sides of said shank section.

10. A staple and thread assembly as claimed in claim 3, wherein said shank section is offset with respect to said head section on both sides of said shank section.

11. A staple and thread assembly as claimed in in claim 3, wherein said thread is secured to said shank section closer to the pointed tip of said head section than to said rear end of said shank section.

12. A staple and thread assembly as claimed in claim 1, wherein said staple is made of a shape memory alloy which is substantially straight at room temperature, and curved when heated by human body temperature.

13. A staple and thread assembly as claimed in claim 3, wherein said staple is made of a shape memory alloy which is substantially straight at room temperature, and curved when heated by human body temperature.

14. A staple and thread assembly as claimed in claim 12, wherein said shape memory alloy is in the martensitic state at approximately room temperature and transforms to the austenitic state when heated to approximately human body temperature.

15. A staple and thread assembly as claimed in claim 13, wherein said shape memory alloy is in the martensitic state at approximately room temperature and transforms to the austenitic state when heated to approximately human body temperature.

* * * * *

UNITED STATES PATENT AND TRADEMARK OFFICE
CERTIFICATE OF CORRECTION

PATENT NO. : 5,873,891
DATED : Feb. 23, 1999
INVENTOR(S) : Ze'ev Sohn

It is certified that error appears in the above-identified patent and that said Letters Patent is hereby corrected as shown below:

Claim 1 should read as follows:

1. A staple and thread assembly for use in medical suturing, comprising:
a staple having a head section having a longitudinal axis, LAa, and a shank section having a longitudinal axis LAs, said head section being at said staple's forward end and being formed with a pointed tip for penetrating a bone when driven into the bone, said shank section being located immediately rearwardly of said head section, said LAa of said head section being laterally offset from said LAs of said shank section such that said head section assymetrically overhangs said shank section when said staple is driven into the bone.

Signed and Sealed this

Third Day of August, 1999

Attest:

Attesting Officer

Q. TODD DICKINSON

Acting Commissioner of Patents and Trademarks